(12) United States Patent
Lewis

(10) Patent No.: US 11,337,489 B2
(45) Date of Patent: May 24, 2022

(54) MODULAR ORTHOTIC FOOTWEAR SYSTEM

(71) Applicant: Jeff Lewis, London (CA)

(72) Inventor: Jeff Lewis, London (CA)

(73) Assignee: Jeff Lewis, London (CA)

( * ) Notice: Subject to any disclaimer, the term of this patent is extended or adjusted under 35 U.S.C. 154(b) by 0 days.

(21) Appl. No.: 15/931,203

(22) Filed: May 13, 2020

(65) Prior Publication Data
US 2020/0268099 A1 Aug. 27, 2020

Related U.S. Application Data

(63) Continuation-in-part of application No. PCT/CA2018/051434, filed on Nov. 13, 2018.

(60) Provisional application No. 62/585,240, filed on Nov. 13, 2017.

(51) Int. Cl.
| | | |
|---|---|---|
| A43B 3/24 | (2006.01) | |
| A43B 13/18 | (2006.01) | |
| A43B 13/16 | (2006.01) | |
| A43B 13/28 | (2006.01) | |
| A43B 13/30 | (2006.01) | |
| A43B 1/00 | (2006.01) | |
| A43B 17/18 | (2006.01) | |

(52) U.S. Cl.
CPC ............ *A43B 13/186* (2013.01); *A43B 3/246* (2013.01); *A43B 13/16* (2013.01); *A43B 13/28* (2013.01); *A43B 13/30* (2013.01); *A43B 1/0009* (2013.01); *A43B 1/009* (2013.01); *A43B 17/18* (2013.01)

(58) Field of Classification Search
CPC ........... A43B 3/24; A43B 3/244; A43B 3/246; A43B 7/142; A43B 7/1465; A43B 7/144; A43B 13/36; A43B 13/30; A43B 17/006; A43B 13/186; A43B 13/16
USPC ................................. 36/100, 101, 15, 88, 42
See application file for complete search history.

(56) References Cited

U.S. PATENT DOCUMENTS

| | | | | |
|---|---|---|---|---|
| 2,139,885 A | * | 12/1938 | Enrico ................... | A43B 21/36 36/42 |
| 2,185,526 A | * | 1/1940 | Silver .................... | A43B 7/142 36/163 |
| 3,318,026 A | * | 5/1967 | Antelo ................... | A43B 21/37 36/42 |

(Continued)

FOREIGN PATENT DOCUMENTS

| | | |
|---|---|---|
| CN | 101584510 A | 11/2009 |
| DE | 4329186 | 3/1995 |

(Continued)

*Primary Examiner* — Marie D Bays

(74) *Attorney, Agent, or Firm* — Brion Raffoul

(57) ABSTRACT

An orthotic footwear system including a removable outsole, a removable reinforced hollow midsole attached to the top of the outsole, and a removable insole attached to the top of the midsole. A removable metatarsal pad can be attached to the top of the insole, and removable support inserts can be attached around the insole for additional support of problematic areas. Support inserts can be used to support the arch area, the heel area, or both. Each of the removable parts can be interchanged with parts of the same type having different ergonomic characteristics. The user can change the parts of the orthotic to suit their needs. Further, the support inserts can be used apart from the rest of the system, with any insole configured to receive them.

4 Claims, 15 Drawing Sheets

(56) References Cited

U.S. PATENT DOCUMENTS

| | | | | |
|---|---|---|---|---|
| 4,279,083 A * | 7/1981 | Dilg | A43B 13/36 | 36/101 |
| 4,316,333 A * | 2/1982 | Rothschild | A43B 7/142 | 36/50.1 |
| 4,409,745 A * | 10/1983 | Musci | A43B 7/142 | 12/142 J |
| 4,463,505 A | 8/1984 | Duclos | | |
| 4,805,320 A * | 2/1989 | Goldenberg | A43B 1/0054 | 36/36 R |
| 4,813,157 A * | 3/1989 | Boisvert | A43B 7/142 | 36/145 |
| 4,841,648 A * | 6/1989 | Shaffer | A43B 7/1465 | 36/145 |
| 4,843,741 A | 7/1989 | Yung-Mao | | |
| 4,845,863 A | 7/1989 | Yung-Mao | | |
| 4,905,382 A | 3/1990 | Yung-Mao | | |
| 4,908,962 A | 3/1990 | Yung-Mao | | |
| 5,138,774 A * | 8/1992 | Sarkozi | A43B 7/14 | 36/159 |
| 5,154,682 A * | 10/1992 | Kellerman | A43B 1/0072 | 36/44 |
| 5,174,049 A * | 12/1992 | Flemming | A43B 1/0009 | 36/28 |
| 5,400,528 A | 3/1995 | Skinner et al. | | |
| 5,692,322 A * | 12/1997 | Lombardino | A43B 3/24 | 36/100 |
| 5,822,888 A | 10/1998 | Terry | | |
| 6,023,857 A | 2/2000 | Vizy et al. | | |
| 6,092,311 A * | 7/2000 | MacNamara | A43B 1/0036 | 36/100 |
| 6,205,685 B1 * | 3/2001 | Kellerman | A43B 1/0072 | 36/160 |
| 6,345,454 B1 | 2/2002 | Cotton | | |
| 6,408,543 B1 * | 6/2002 | Erickson | A43B 3/26 | 36/100 |
| 6,449,878 B1 | 9/2002 | Lyden | | |
| 6,732,457 B2 * | 5/2004 | Gardiner | A43B 7/141 | 36/155 |
| 7,111,416 B2 * | 9/2006 | Gallegos | A43B 3/24 | 36/100 |
| 7,219,383 B1 | 5/2007 | Ambrosini | | |
| 7,246,453 B2 * | 7/2007 | Kim | A43B 5/00 | 36/100 |
| 7,254,905 B2 * | 8/2007 | Dennison | A43B 7/18 | 36/15 |
| 7,600,332 B2 * | 10/2009 | Lafortune | A43B 7/1465 | 36/43 |
| 7,793,428 B2 | 9/2010 | Shenone | | |
| 7,950,167 B2 * | 5/2011 | Nakano | A43B 13/186 | 36/28 |
| 7,950,168 B2 * | 5/2011 | Nakano | A43B 21/433 | 36/28 |
| 8,205,357 B2 | 6/2012 | Keating et al. | | |
| 8,381,416 B2 | 2/2013 | Geer et al. | | |
| 8,435,346 B2 | 5/2013 | Matsumura et al. | | |
| 8,789,253 B2 | 7/2014 | Kilgore et al. | | |
| 9,107,472 B2 * | 8/2015 | Donzis | A43B 7/1445 | |
| 9,788,602 B2 * | 10/2017 | Wynn | A43B 13/188 | |
| 2003/0200675 A1 * | 10/2003 | Gross | A43B 13/20 | 36/15 |
| 2003/0200676 A1 * | 10/2003 | Gross | A43B 13/36 | 36/15 |
| 2004/0194351 A1 * | 10/2004 | Gallegos | A43B 3/24 | 36/140 |
| 2005/0120589 A1 * | 6/2005 | Coomes | A43B 3/0078 | 36/15 |
| 2006/0059726 A1 * | 3/2006 | Song | A43B 7/1435 | 36/142 |
| 2007/0186446 A1 * | 8/2007 | Lafortune | A43B 13/40 | 36/43 |
| 2007/0277401 A1 * | 12/2007 | Young-Chul | A43B 13/186 | 36/30 R |
| 2008/0196272 A1 * | 8/2008 | Hay | A43B 13/186 | 36/88 |
| 2008/0222920 A1 * | 9/2008 | Rovida | A43B 5/18 | 36/100 |
| 2009/0133288 A1 * | 5/2009 | Gallegos | A43B 13/223 | 36/91 |
| 2010/0186265 A1 * | 7/2010 | Evans | A43B 13/184 | 36/36 R |
| 2010/0269375 A1 | 10/2010 | Georgoulakis | | |
| 2011/0000101 A1 * | 1/2011 | Nakano | A43B 7/144 | 36/12 |
| 2013/0091733 A1 | 4/2013 | Klein | | |
| 2013/0167405 A1 * | 7/2013 | Forsey | A43B 7/1465 | 36/92 |
| 2013/0219744 A1 * | 8/2013 | Case | A43B 7/142 | 36/43 |
| 2013/0312280 A1 * | 11/2013 | Gardiner | A43B 1/0009 | 36/43 |
| 2013/0318818 A1 * | 12/2013 | Gardiner | A43B 7/141 | 36/43 |
| 2013/0333249 A1 * | 12/2013 | Guer | A43B 7/144 | 36/134 |
| 2014/0182170 A1 | 7/2014 | Wawrousek et al. | | |
| 2015/0289588 A1 * | 10/2015 | Kramer | A43B 13/141 | 36/28 |
| 2015/0289594 A1 | 10/2015 | Rushbrook et al. | | |
| 2015/0342295 A1 * | 12/2015 | Moon | A43B 17/023 | 36/43 |
| 2016/0037860 A1 * | 2/2016 | Holt | A43B 13/186 | 36/28 |
| 2016/0324264 A1 | 11/2016 | Johnson | | |
| 2017/0027277 A1 * | 2/2017 | Anthony | A43B 17/02 | |
| 2017/0127758 A1 | 5/2017 | Cooper | | |
| 2018/0140048 A1 * | 5/2018 | Shi | H02J 7/00 | |
| 2019/0116925 A1 | 4/2019 | Darby et al. | | |
| 2020/0107612 A1 * | 4/2020 | Schickling | A43B 7/142 | |
| 2020/0113275 A1 * | 4/2020 | Zuborev | A43B 9/14 | |

FOREIGN PATENT DOCUMENTS

| | | |
|---|---|---|
| EP | 2292114 B1 | 1/2014 |
| WO | 2000054616 A1 | 9/2000 |
| WO | 2001080678 A2 | 11/2001 |
| WO | 2005117629 A1 | 12/2005 |
| WO | 2006031444 A2 | 3/2006 |
| WO | 2017003473 | 1/2017 |

* cited by examiner

MODULAR ORTHOTIC FOOTWEAR SYSTEM

RELATED APPLICATIONS

This application is a continuation-in-part of international patent application no. PCT/CA2018/051434 filed on Nov. 13, 2018, which claims the benefit of U.S. provisional application No. 62/585,240 filed on Nov. 13, 2017.

TECHNICAL FIELD

The present invention relates to orthotic footwear. More specifically, the present invention relates to a customizable orthotic footwear system.

BACKGROUND

Customized orthotics can help improve a user's posture, gait, balance, and overall health. For instance, a common foot condition known as "over-pronation" (in which the arch and ankle roll towards the ground with each step) can have significant adverse effects on wellness, endurance, and comfort. A customized orthotic device that provides extra arch support can correct over-pronation and improve the user's well-being.

Unfortunately, most customized orthotics are custom made and made to order and, as such, are unalterable. They are designed and built by third-party companies, often based on a static mold of the user's foot at one moment in time, and they typically cannot be changed once formed. A user's gait, however, often shifts over time, and, when such a shift occurs, the custom orthotic that was once comfortable no longer provides a benefit. Thus, the user must purchase another expensive device that, again, cannot be adjusted once received.

There are numerous "modular" or "semi-customized" orthotics in the prior art, which attempt to balance customization and cost. Some are "semi-customized" only in that they combine prefabricated parts into a static device, while others allow the user to make adjustments. However, even these devices generally only allow one part of the shoe to be adjusted by a user. As examples, it is known to construct a shoe with an interchangeable midsole (U.S. Pat. No. 8,205,357) or to manufacture an insole with detachable support pads (U.S. Pat. No. 8,435,346). There is not, as yet, a complete orthotic footwear system in which multiple parts of a shoe may be interchanged to suit a user's specific needs.

Moreover, many of the current user-adjustable orthotic devices rely on hook and loop attachment systems (e.g., Velcro™) and other insecure fastening mechanisms that can be easily dislodged by vigorous activity. There is therefore a need for a more durable and secure footwear system that is also versatile and entirely user-configurable.

SUMMARY

The present invention provides an orthotic footwear system comprising a removable outsole, a removable reinforced hollow midsole attached to the top of the outsole, and a removable insole attached to the top of the midsole. A removable metatarsal pad can be attached to the top of the insole, and removable support inserts can be attached under the insole for additional support of problematic areas. Support inserts can be used to support the arch area, the heel area, or both. Each of the removable parts can be interchanged with parts of the same type having different ergonomic characteristics. The user can change the parts of the orthotic device to suit their needs. Further, the support inserts can be used apart from the rest of the system, with any insole configured to receive them.

In a first aspect, the present invention provides a footwear system comprising:
  a sole, said sole comprising:
    an outsole;
    a midsole, said midsole comprising an outer shell and a support structure within the outer shell;
    an insole; and
  an upper;
  wherein said midsole is removably attached to a top side of said outsole and said insole is removably attached to a top side of said midsole, and wherein said upper is removably attached to said sole.

In a second aspect, the present invention provides a support insert, said support insert being for providing support to an arch region of a user's foot or a heel region of a user's foot.

In a third aspect, the present invention provides a kit of parts for assembly into a shoe, the kit comprising:
  a sole, said sole comprising:
    an outsole, selected from a plurality of outsoles, each of said plurality of outsoles having a unique set of ergonomic outsole characteristics;
    a midsole, selected from a plurality of midsoles, each of said plurality of midsoles having a unique set of ergonomic midsole characteristics, and said midsole comprising an outer shell and a lattice of hexagonal ribs a support structure within the outer shell;
    an insole, selected from a plurality of insoles, each of said plurality of insoles having a unique set of ergonomic insole characteristics, and said insole comprising a support layer and a soft upper layer fixedly attached to a top side of the support layer; and
  an upper;
  wherein said midsole is for attachment to a top side of said outsole and said insole is for attachment to a top side of said midsole, and wherein said upper is for attachment to said sole.

BRIEF DESCRIPTION OF THE DRAWINGS

The present invention will now be described by reference to the following figures, in which identical reference numerals refer to identical elements and in which.

DETAILED DESCRIPTION

The present invention provides a versatile and secure footwear system which can be adjusted by the user. An outsole, midsole, and insole, each having specific ergonomic characteristics, can be combined together into an orthotic sole. Additionally, a metatarsal pad can be added on top of the insole, and support inserts may be attached under the insole, at the heel area or arch area of the foot. An upper can then be attached to the sole, to form a complete shoe. As the user's needs change, the shoe can be disassembled and reassembled, using components with different ergonomic characteristics, to produce a different shoe. This versatile system represents a significant cost-savings for the user over traditional custom orthotics. As an example, if a user's gait changes such that the user needs a firmer insole, the user only needs to purchase a firmer insole. Then, using the firmer insole and the components from his currently owned shoe, the user can construct a shoe that is more directed towards his current needs.

Figure 1:
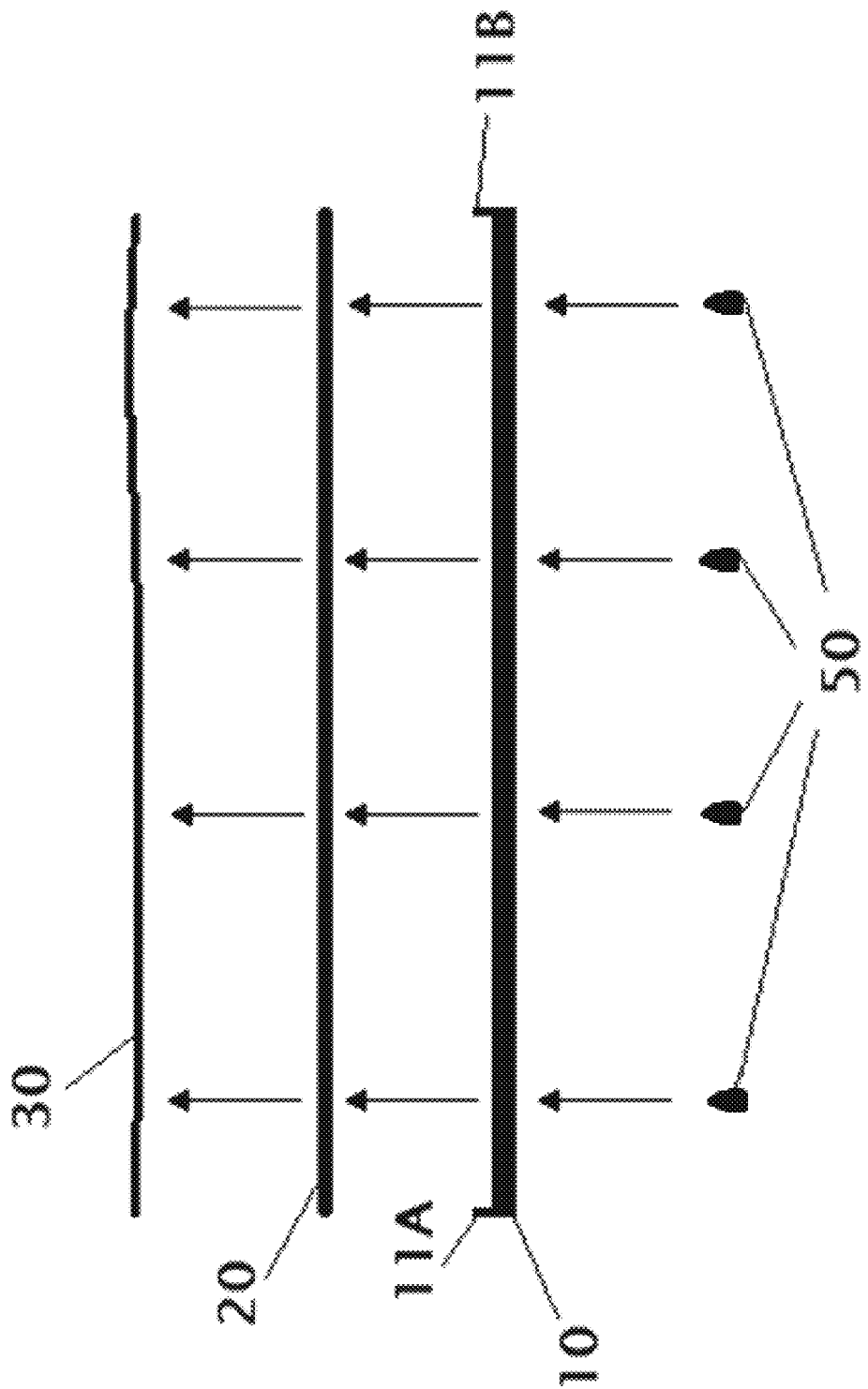
FIG. 1 is an exploded schematic diagram showing a side view of an orthotic footwear system according to one embodiment of the invention.

FIG. 1 is an exploded schematic diagram showing a side view of one embodiment of the orthotic system. (Note that FIGS. 1 to 4 are not to scale.) An outsole 10 forms the base of the shoe. Vertical segments 11A and 11B project from the rim of the outsole 10, at the heel end and toe end. (For reference, the toe end of the shoe is located at the left side of FIG. 1, and the heel end is located at the right side of the figure.) A midsole 20 fits on top of the outsole 10 and will fit between these projections 11A and 11B. The projections 11A and 11B provide extra support for the frame of the shoe.

An insole 30 fits on top of the midsole 20. The outsole 10, the midsole 20, and the insole 30 are attached to each other by a plurality of screws 50. Note that the use of four screws 50 in FIG. 1 is only intended as an example: any sufficient number of screws 50 may be used. The screws 50 pass upwards through the shoe in the direction of the arrows. When the screws 50 are tightly fastened, the screw heads are secure in the outsole 10 and the all portions of the sole are securely attached to one another.

It should be clear that any appropriate fastening mechanism may be used instead of the screws 50, including, for example, nuts and bolts, clips, or tacks.

Figure 2:
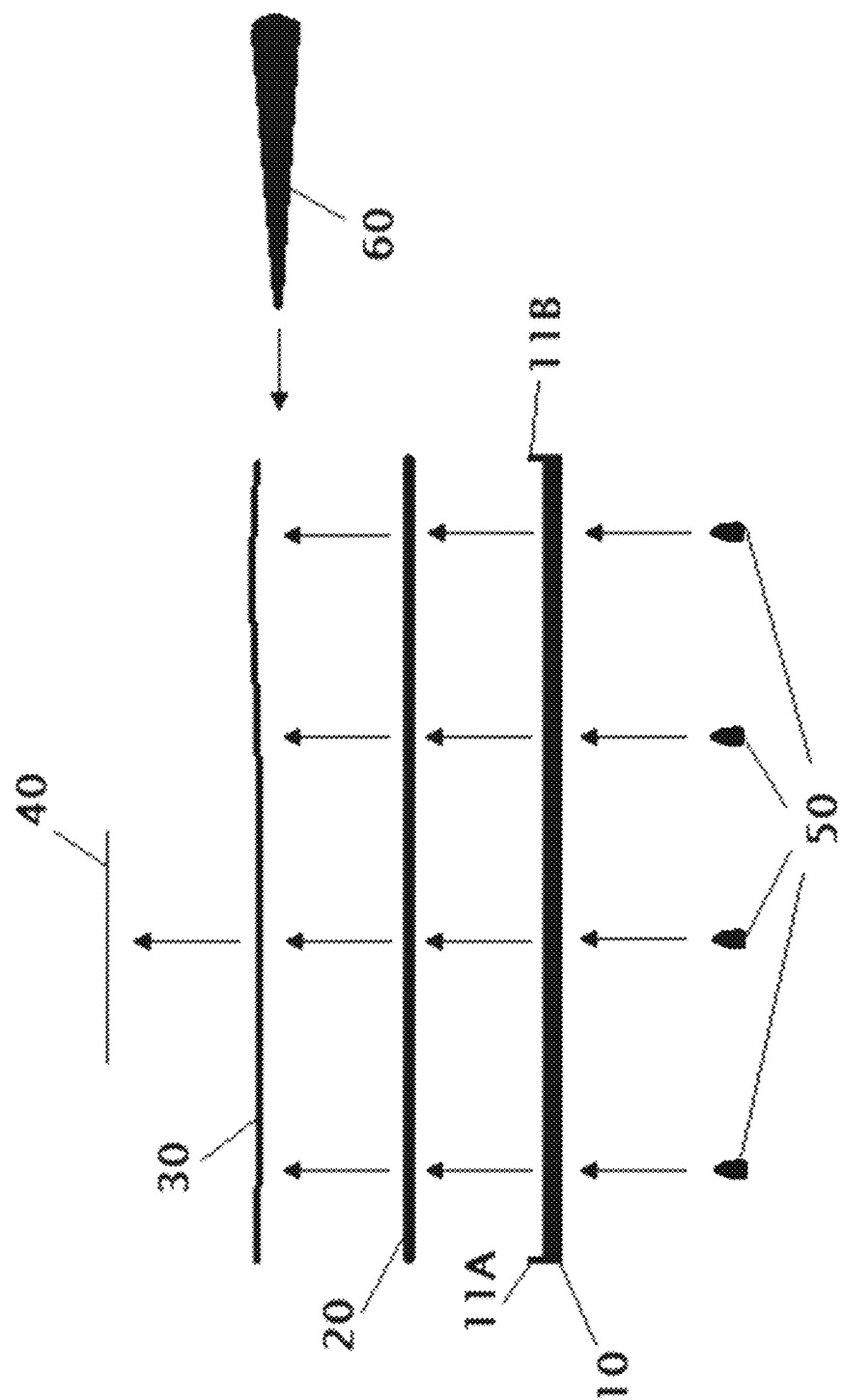
FIG. 2 is an exploded schematic diagram showing a side view of an orthotic footwear system according to another embodiment of the invention.

FIG. 2 shows an exploded schematic diagram according to another embodiment of the invention. In the embodiment shown, a metatarsal pad 40 fits on top of the insole, near the toe end of the shoe. The metatarsal pad 40 is attached to the rest of the sole using the same screws 50 that attach the outsole 10, midsole 20, and insole 30 to each other.

It should be noted that the metatarsal pad 40 is not a required component of the invention. The metatarsal pad 40 can be attached to the insole, if the user finds it beneficial, or it can be left off if that is preferable.

Additionally, the embodiment of the invention shown in FIG. 2 shows a heel support insert 60 (again, this figure is not to scale). This heel support insert 60 attaches to the underside of the insole 30 and lifts the heel end of the insole 30 to provide extra support for the user's heel.

Figure 3:
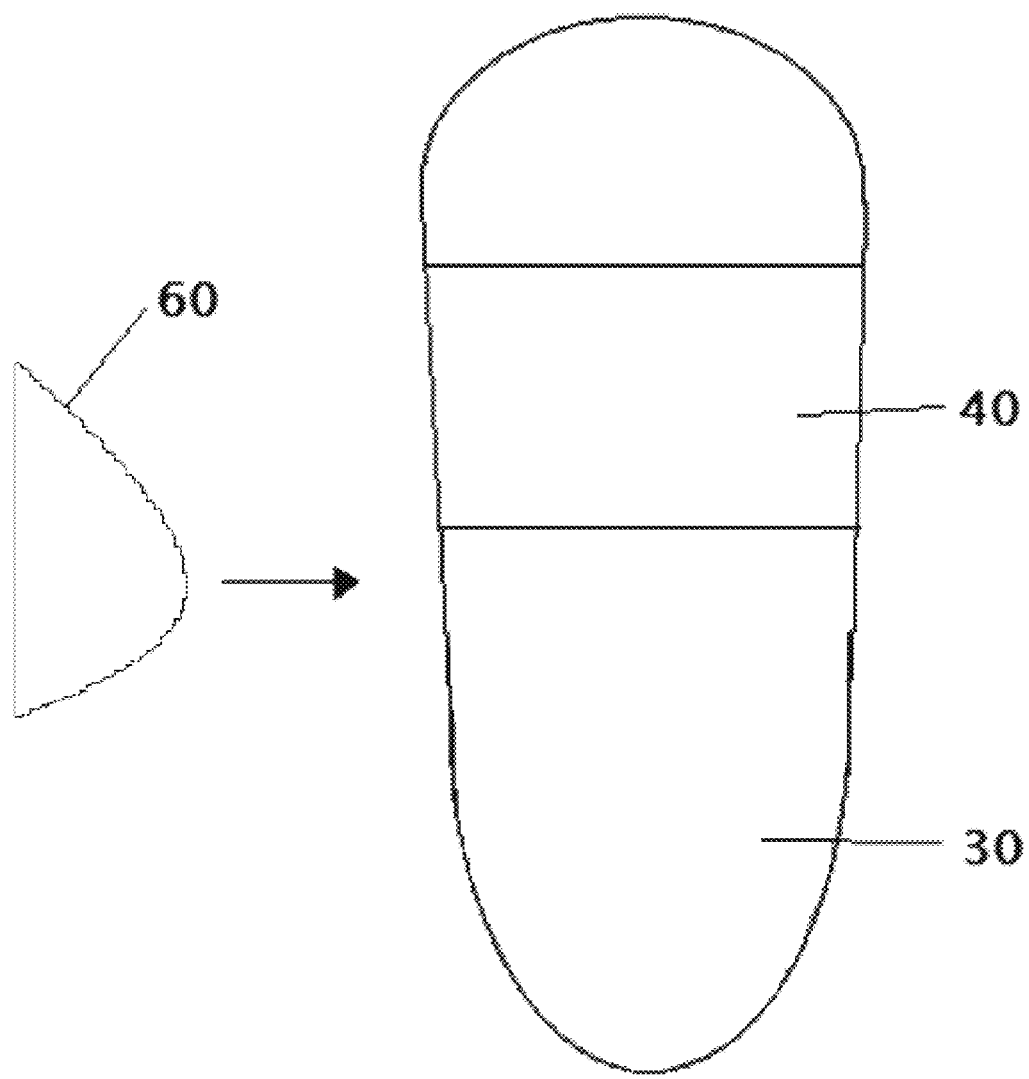
FIG. 3 is a schematic diagram showing a top view of an orthotic footwear system according to a third embodiment of the invention.

FIG. 3 is a diagram showing a top view of another embodiment of the invention, which uses an arch support insert 60 rather than a heel support insert. For clarity, it should be noted that the screws 50 are not visible from this angle. A metatarsal pad is also used in this embodiment: as can be seen from the Figure, metatarsal pad 40 is attached to the top side of the insole 30. The outsole, midsoles, and the fastening screws are not visible in this view. (Again, FIG. 3 is not to scale.)

In this embodiment of the invention, an arch support insert 60 is shown on the medial side of the foot (that is, on the side closest to the other foot). The support insert 60 provides support to the arch region of the foot and may help correct or prevent over-pronation, among other conditions.

Figure 4:
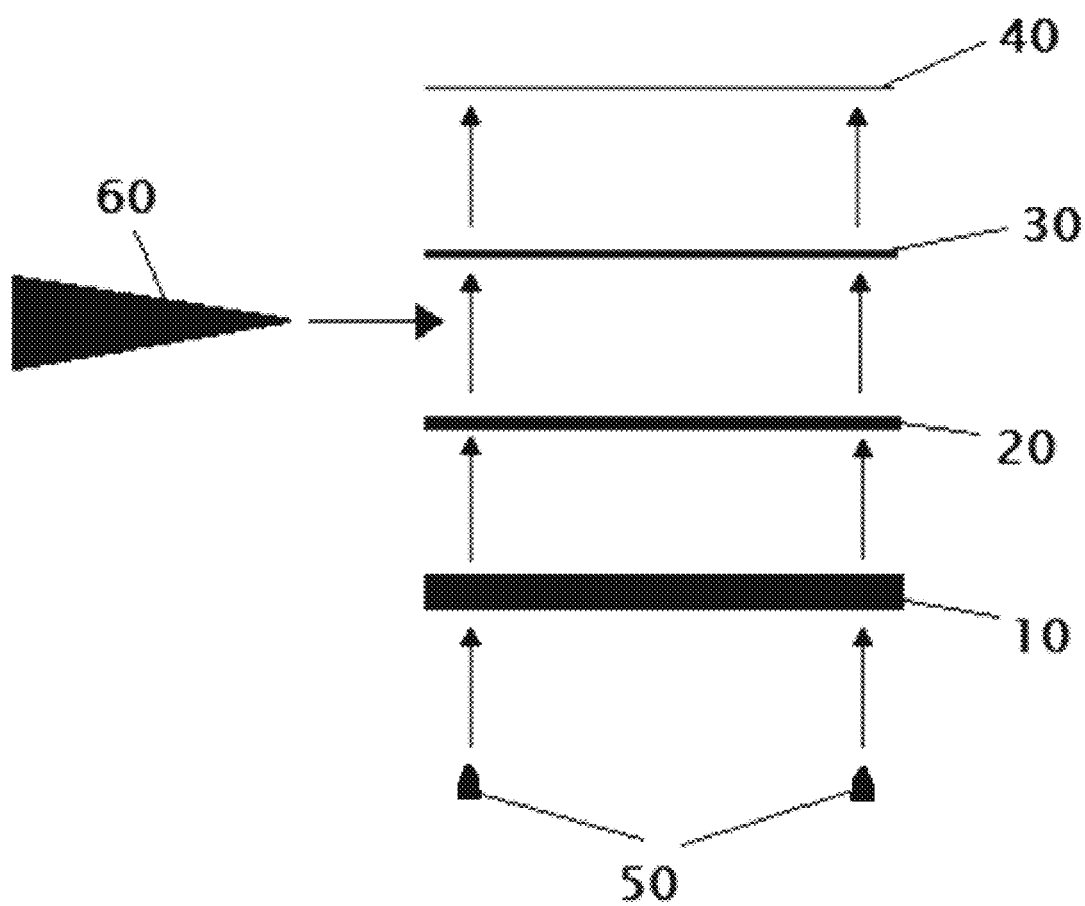
FIG. 4 is an exploded schematic diagram showing a side view of the orthotic footwear system illustrated in FIG. 3.

FIG. 4 is a schematic diagram showing the embodiment of the invention of FIG. 3, from a perspective along the shoe from heel to toe. That is, it is a rear view of a right shoe with the medial side of the shoe at the left of the page. (Note again that FIG. 4 is not to scale.) The screws 50 fasten together the outsole 10, the midsole 20, the insole 30, and the metatarsal pad 40. The support insert 60 attaches to the underside of the insole 30, and provides arch support.

Figure 5:
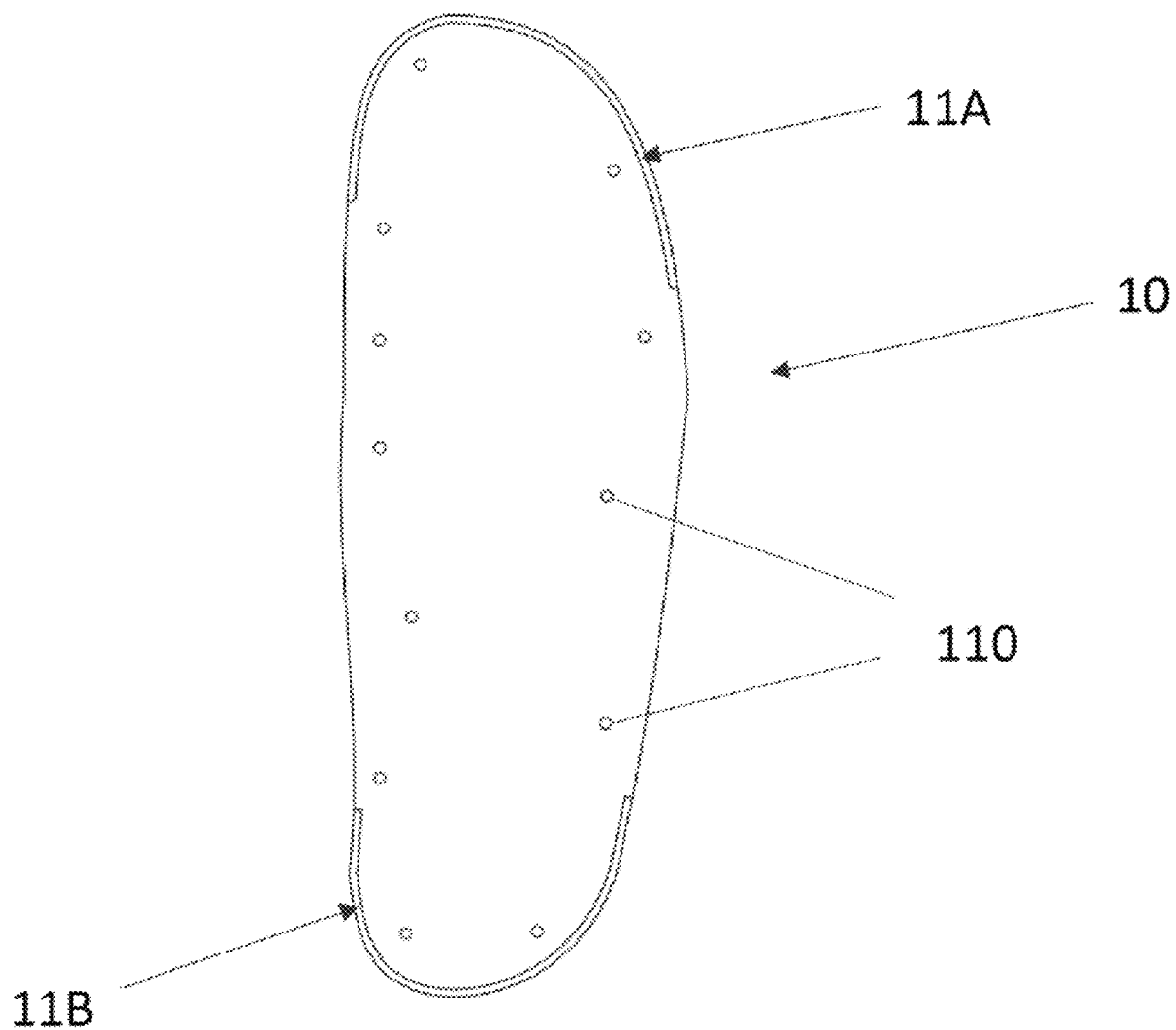
FIG. 5 shows an outsole according to one embodiment of the invention.

FIG. 5 is an image of an outsole 10 by itself. Multiple screw holes 110 are provided around the edges of the outsole 10, and vertical segments 11A and 11B project from the rim at the toe and heel ends of the outsole 10.

The upper side of the outsole 10, visible in FIG. 5, is a smooth and flat surface.

The outsole 10 is made of a flexible but durable material. As an example, a polymer such as polypropylene may be used to manufacture the outsole. Other kinds of polymers, or natural materials that are both sturdy and flexible, can also be used.

Many variations of the outsole are possible. For example, a user may select an outsole that has a lift of as little as 1 mm or as much as 1 cm. Alternatively, a user may select an outsole having a lateral wedge or having a medial wedge, or having sections made of a firmer material to provide extra support in problem areas. It should be clear that many other variations are possible and that a user may combine any and all such modifications as needed.

Figure 6:
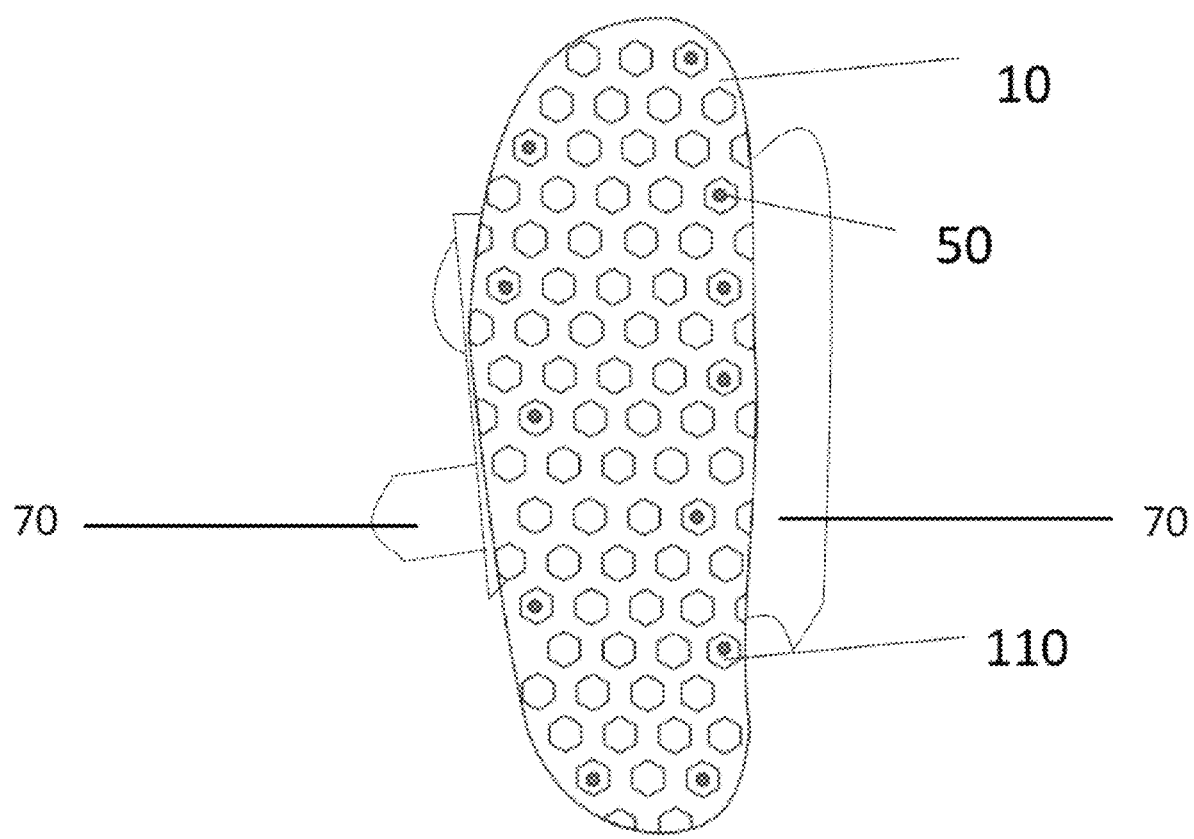
FIG. 6 shows a bottom view of a fully assembled shoe according to one embodiment of the invention.

FIG. 6 is a bottom view of a fully assembled shoe, according to one embodiment of the invention. This image shows primarily the underside of the outsole 10. While the outsole 10 in FIG. 6 has a hexagonal tread, any tread pattern may be used. It should be clear that some embodiments may use an outsole that is smooth on both sides (i.e., an outsole without a tread).

The screws 50 pass through the screw holes 110. It should be noted the screw holes 110 are, on the bottom side of the outsole 10, countersunk such that the screws do not protrude from the plane of the tread and that, as a result, the heads of the screws are recessed from the plane of the tread. The heads of the screws 50 therefore do not interfere with a user's balance and they are also protected from wear.

For additional security, small elongated structures are provided on the upper side of the outsole and the underside of the midsole. These structures have a male-female design: a male portion clips into a corresponding female portion and help maintain a secure attachment between the midsole and the outsole.

FIG. 6 also shows an attached upper 70. In this figure, the upper 70 is a set of sandal straps. The ends of these straps pass between the midsole 20 and the insole 30 and are secured by the same screws 50 that connect the sole parts together. The upper 70 can be made of a polymer, such as ethylene vinyl acetate (EVA), or of a natural material such as leather, or of any combination of synthetic and natural materials.

Moreover, it should be clear that the upper 70 can be any suitably configured shoe upper. Thus, a user may configure any style of footwear using the present invention. A user can thus configure the components to create a formal Oxford-type shoe, a breathable athletic shoe, a soft casual slipper, or any other type of suitable footwear desired by the user. A weatherized upper can also be attached, and, the security of the attachment, will render the footwear at least partly impervious to water and snow. This level of versatility represents an enormous cost-savings for the user. Rather than buying specially designed orthotic versions of each style of footwear that a user desires, the user can simply configure a comfortable orthotic sole and attach a suitable upper to result in a shoe that meets their needs.

Figure 7:
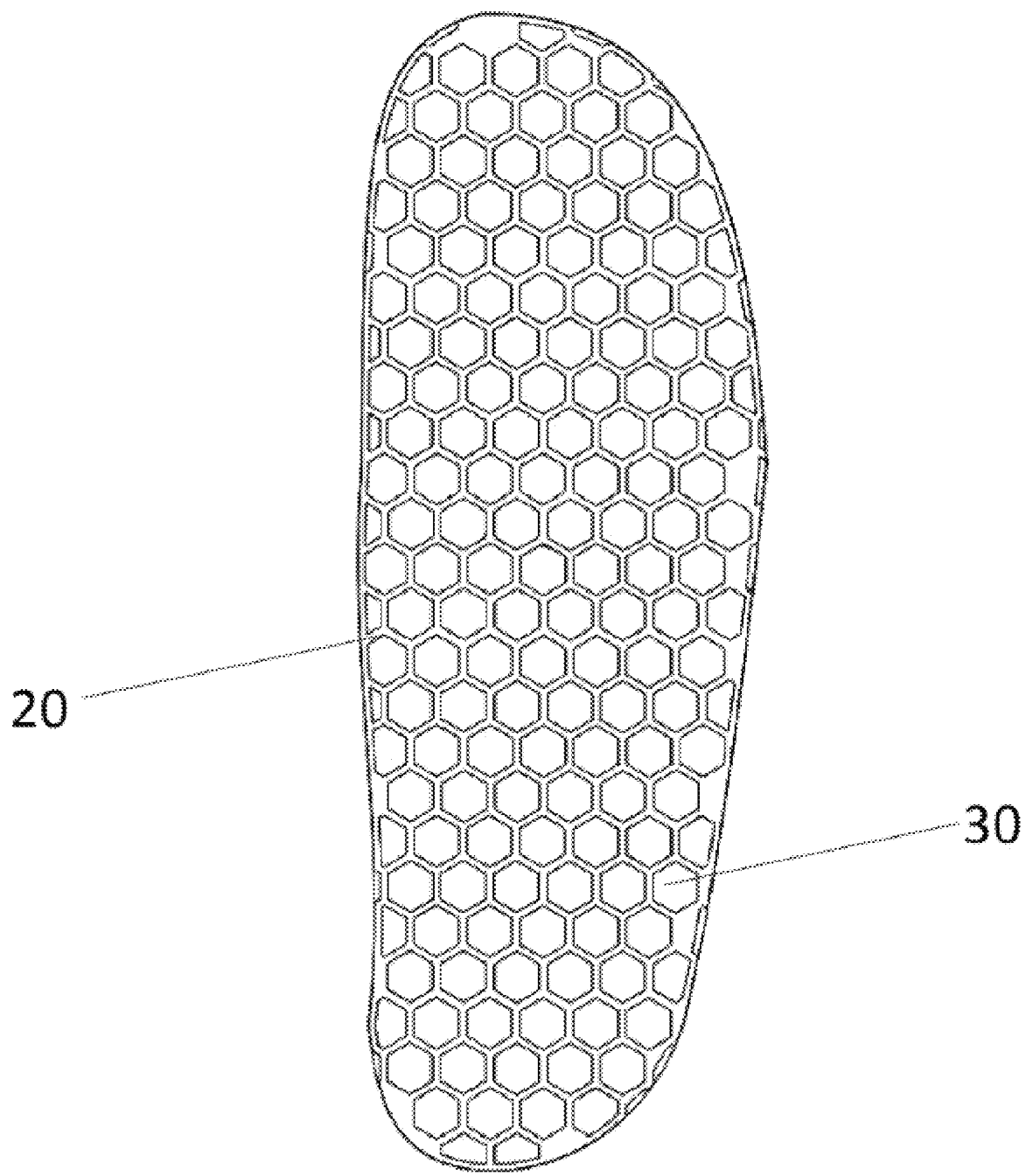
FIG. 7 shows a bottom view of a midsole and an insole according to one embodiment of the invention.

FIG. 7 shows a bottom view of a midsole 20 and an insole 30 according to one implementation of the invention. In this implementation, the midsole 20 is mostly hollow to reduce the overall weight of the shoe and is reinforced with hexagonal ribs. The ribs support the midsole and allow even distribution of the user's weight. The midsole 20 can be made of a polymer such as ethylene vinyl acetate (EVA), or of suitably durable natural materials (e.g., hardened rubber). The outer edge of the midsole 20 is reinforced with a layer of another durable material, such as polypropylene, to help maintain its shape.

In one implementation, the insole 30 is made of two layers. The upper layer can be made from a soft, flexible polymer, for the user's comfort, or from similar natural or synthetic materials. The underside of the insole 30, however, is reinforced with hard material, such as that used to form the midsole. Alternatively, the underside could be reinforced using any suitably sturdy material. This reinforcement helps to distribute weight and increases durability for the insole. The screw holes 110 are also reinforced—the reinforcement protects against wear and helps prevent the screw holes from tearing due to sudden stress or repeated use.

Figure 8:
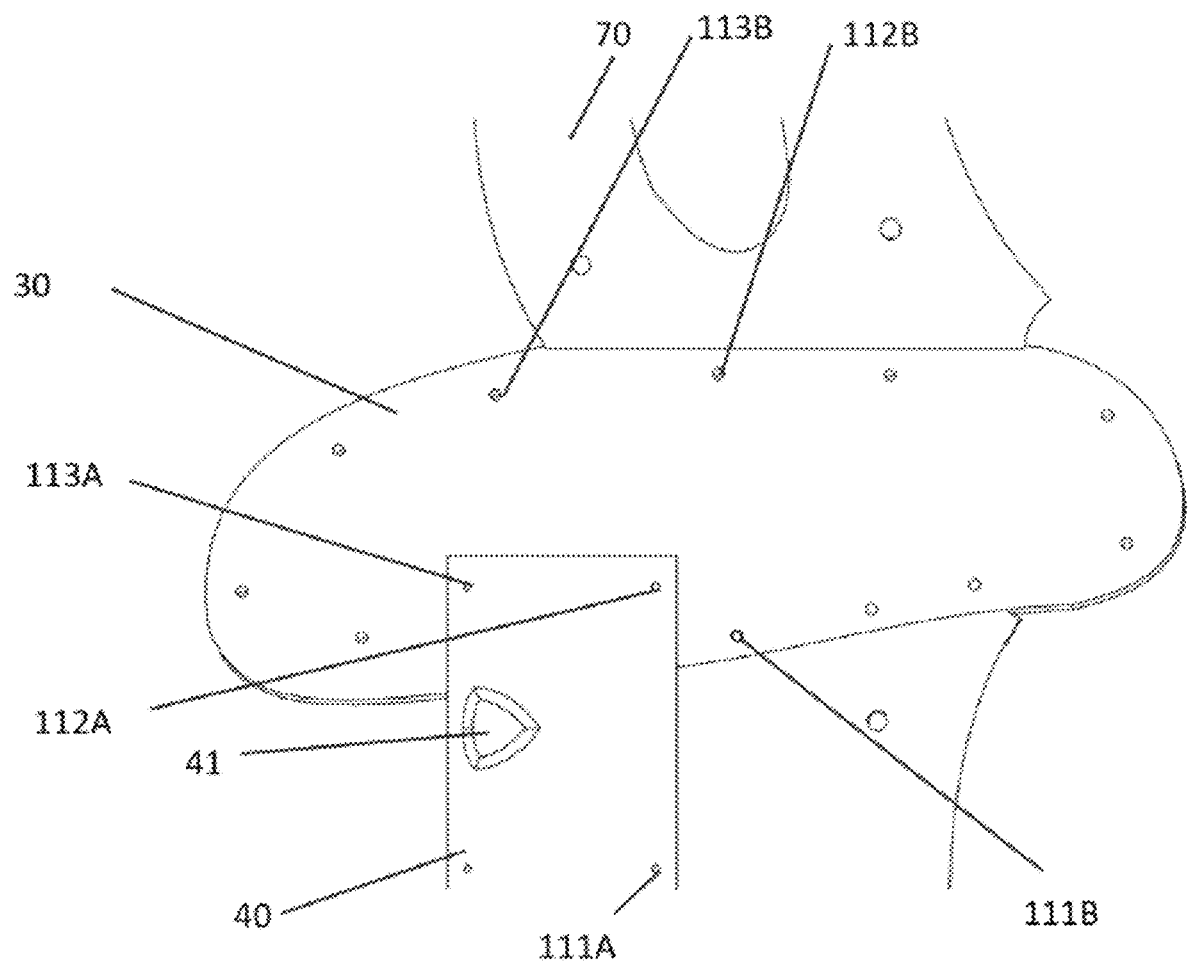
FIG. 8 shows a top view of a partially assembled shoe according to one embodiment of the invention.

FIG. 8 shows a partially assembled shoe, according to one embodiment of the invention. FIG. 8 is a top view of a right-footed shoe, showing the insole 30, the metatarsal pad 40, and the upper 70. As can be seen, a central portion of the insole 30 is configured to receive the metatarsal pad 40. Further, screw holes 111A, 112A, 113A on the metatarsal pad 40 align with corresponding screw holes 111B, 112B, 113B on the insole 30.

The metatarsal pad 40 has a pad portion (referred to in FIG. 8 by reference number 41). This raised pad portion 41 is roughly teardrop-shaped. When the metatarsal pad 40 is attached to the rest of the shoe, the point of the teardrop shape points towards the heel and the pad portion 41 provides support under the second, third, and fourth metatarsal bones of the user's foot. This area of the foot often benefits from the cushioning provided by a raised pad.

Figure 9:
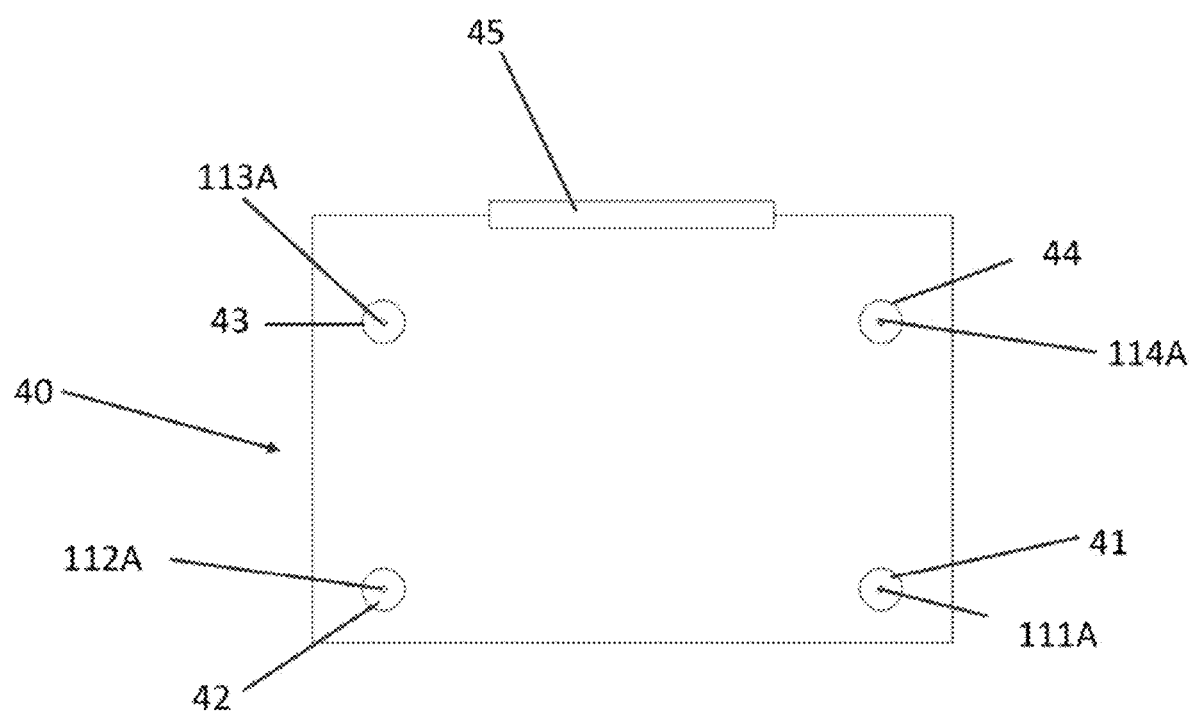
FIG. 9 shows a bottom view of a metatarsal pad according to one embodiment of the invention.

FIG. 9 shows the underside of a metatarsal pad 40. As can be seen, each of the screw holes 111A, 112A, 113A, and 114A is surrounded by a corresponding locator bushing (41, 42, 43, or 44). The locator bushings 41-44 help to protect the screw holes 111A-114A from wear and, additionally, help guide the screws 50 through the holes. Locator protrusion 45 helps to fit the metatarsal pad 40 onto an insole 30, attaching the pad to the insole and allowing and allowing easy proper positioning of the metatarsal pad 40 on the insole.

The metatarsal pad 40 has the same two-layer structure as the insole 30: a softer upper layer for comfort affixed to a sturdier lower layer with the lower layer reinforcing the insert and helping distribute weight over the ribs of the midsole 20 below.

Figure 10:
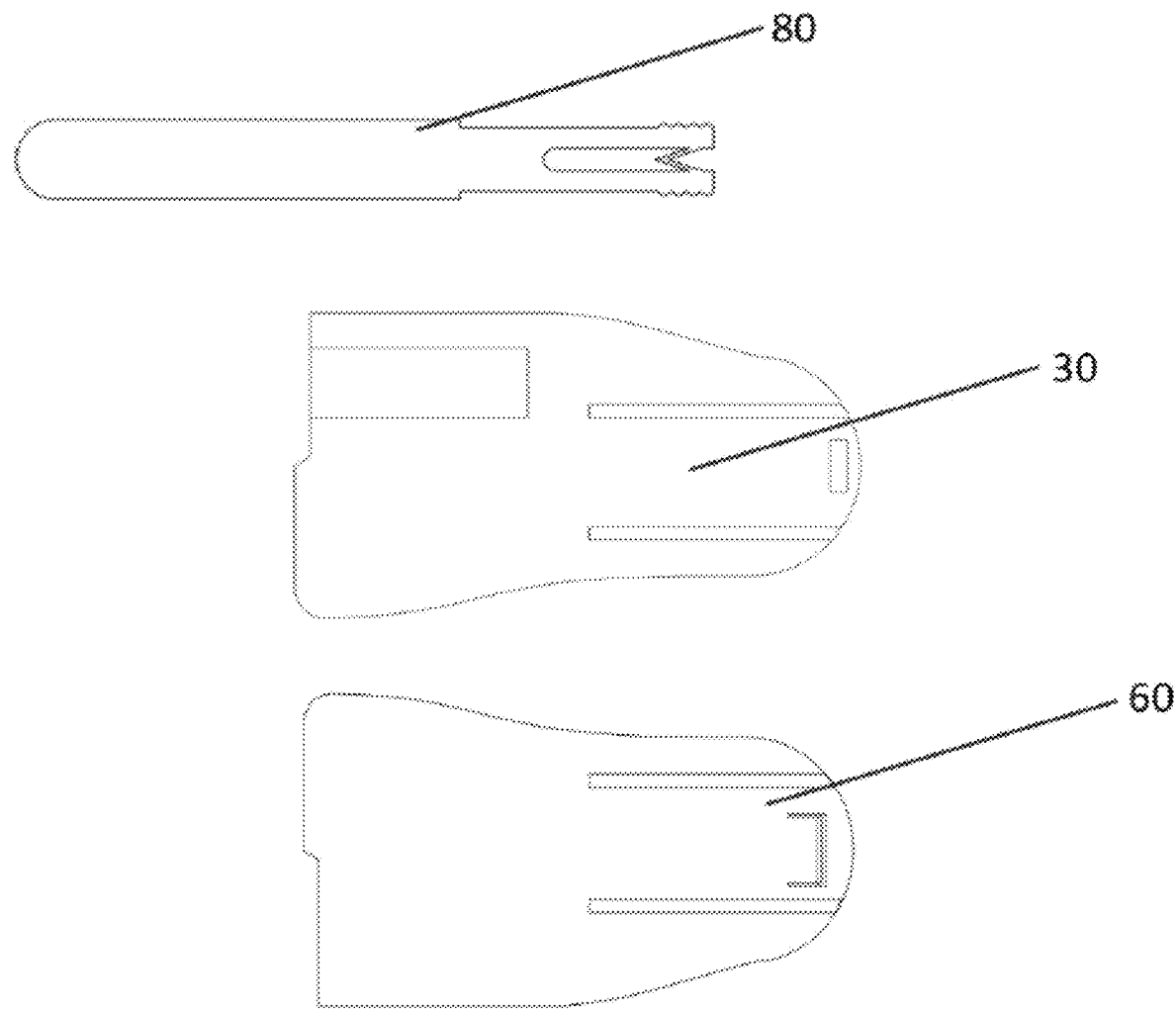
FIG. 10 shows a modified insole, a support insert, and an extension piece according to one embodiment of the invention.
Figure 11:
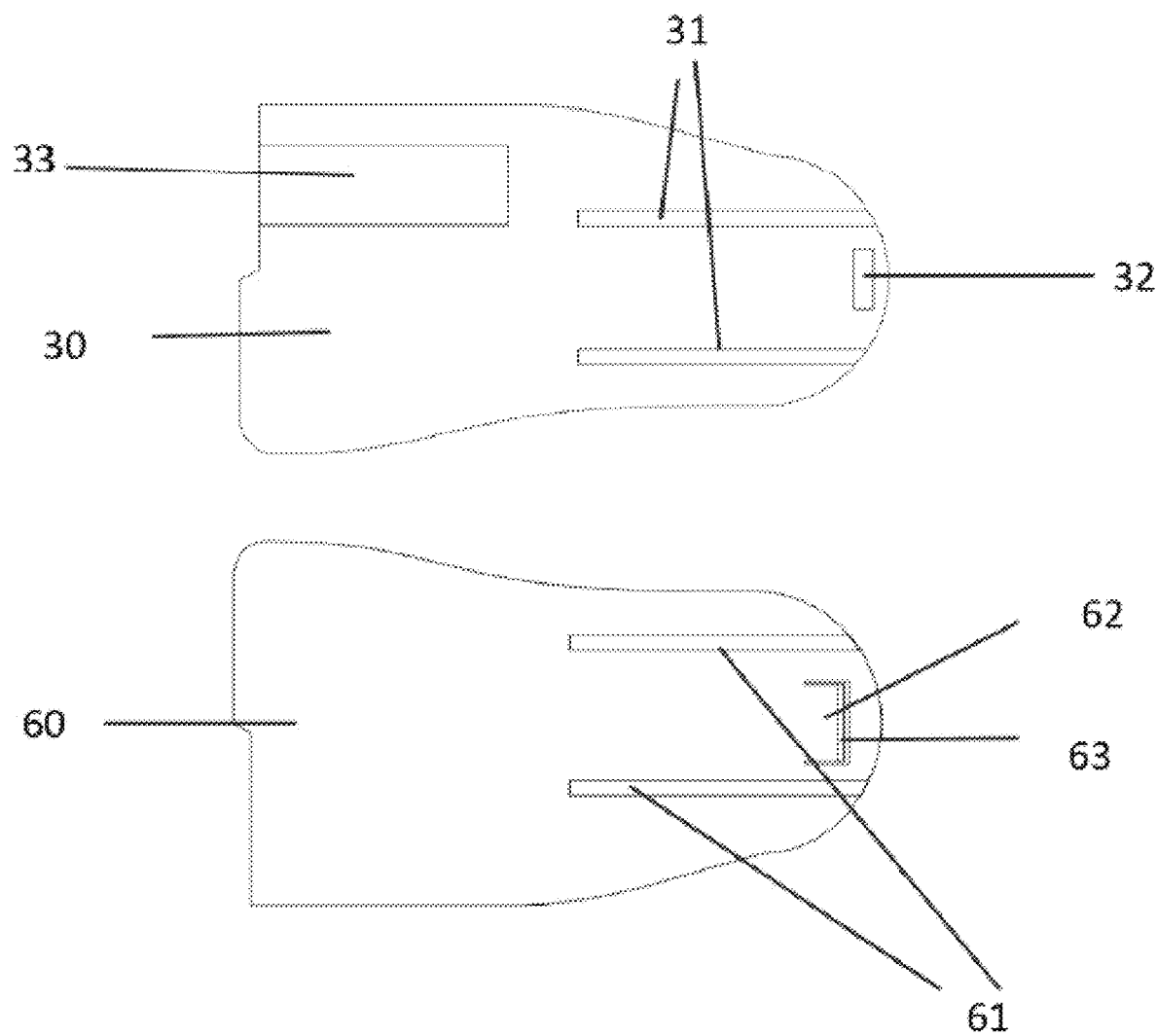
FIG. 11 shows the modified insole and support insert of FIG. 10.

FIG. 10 shows the underside of a half-insole 30, modified to accept a heel lift support insert 60, and an extension piece 80. Note that the example insole shown is a half-insole. It should be clear that full-sized insoles can be similarly modified to accept heel lift support inserts, or to accept arch support inserts. Note also that this modified insole 30 is for a right-footed shoe. FIG. 11 shows the modified insole 30 and support insert 60 in more detail.

Attachment grooves 31 are formed in the underside of the modified insole 30, as can be seen in FIG. 11. As should be clear, these attachment grooves may be formed to any length, width, and depth, as necessary to accommodate the desired support insert. In the embodiment shown, the grooves 31 begin at the heel and are oriented towards the toe, as the support insert 60 shown is a heel clip.

The support insert 60 has attachment tracks 61 formed on its upper side. These attachment tracks 61 are formed to fit into and cooperate with the attachment grooves 31 of the modified insole 30. For additional security, a securing mechanism 62 having a catch 63 cooperates with a recess 32 on the underside of the modified insole 30, to prevent unwanted motion of the support insert 60. When the securing mechanism is engaged, the catch 63 on the mechanism 62 protrudes into and is captured by the recess 32, thereby preventing unwanted and undue movement or slippage of the support insert 60 relative to the insole 30.

Figure 12:
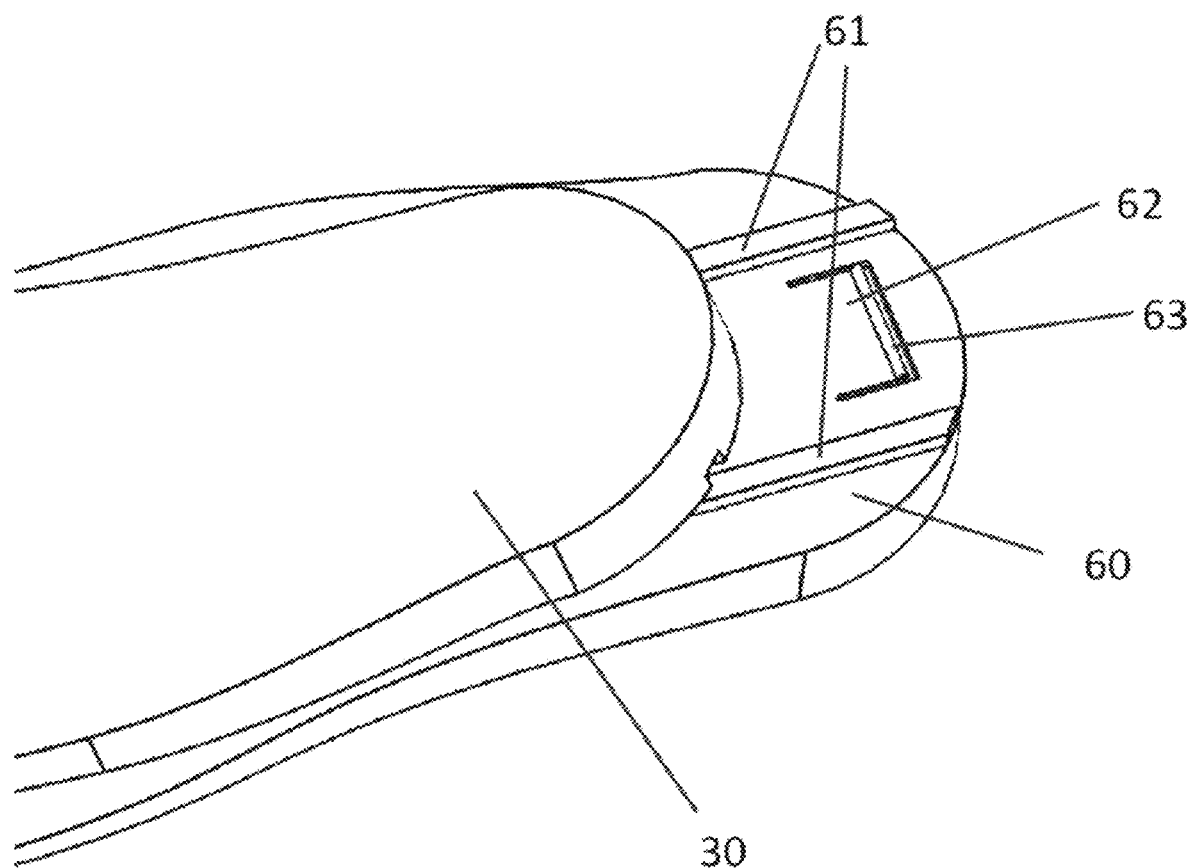
FIG. 12 shows the modified insole and support insert of FIG. 10 with the support insert partially attached to the insole.

FIG. 12 shows the support insert 60 about to be attached to the underside of a modified insole 30. As can be seen, the clip 60 slides underneath the insole 30 with the tracks 61 being engaged in the grooves 31. The attachment tracks 61 slidably fit into grooves on the underside of the insole 30, until the catch 63 on the securing mechanism 62 protrudes into and is captured by the recess 32.

Figure 13:
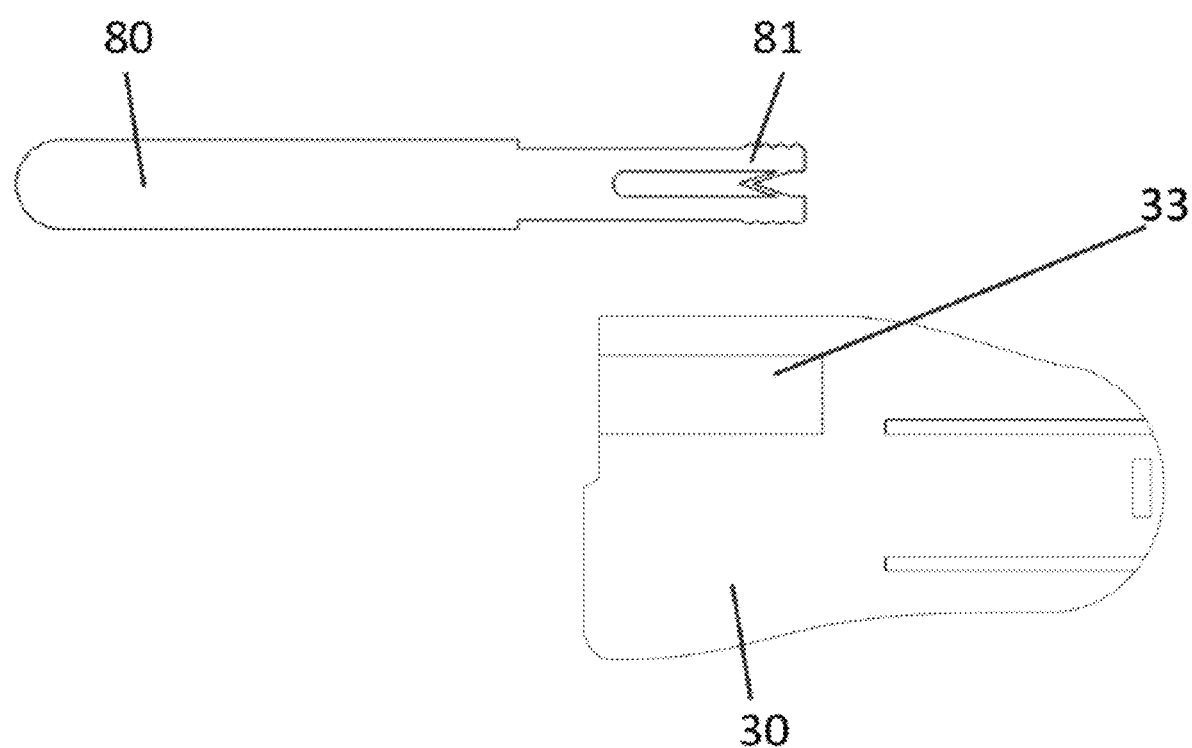
FIG. 13 shows the modified insole and extension piece of FIG. 10 in greater detail.

FIG. 13 shows the underside of modified half-insole 30 and an extension piece 80. The extension piece provides support to the first ray of the foot. "The first ray" is a well-known term in the field that refers to the area of the foot under the great toe and first metatarsal. The first ray is often ergonomically problematic and frequently benefits from additional support. Thus, an extension piece 80 is provided to add support for the first ray when a half-insole is used.

The extension piece 80 connects to the modified insole 30 by means of an expandable brace (shown as 81 in FIG. 13). A receiving groove 33 is formed in the underside of the modified insole 30. The user, attaching the extension piece, compresses the spring portion of the brace 81 and inserts the brace 81 into the receiving groove 33. When the user releases the brace 81, the spring portion expands and the outside teeth of the brace catch the sides of the receiving groove 33 and connect with the groove walls. The friction between the teeth of the brace 81 and the groove walls secures the connection.

It should be noted that though the modified insole 30 shown in FIGS. 10 to 13 is a half insole, a full insole can easily be modified to have a catch and attachment grooves, to accommodate a support insert. However, as a full insole will by default support the first ray of the foot, modifications to accommodate an extension piece may not be necessary.

Further, the insole modifications needed for an arch support insert will be generally similar to those used for a heel support insert: attachment grooves and tracks, and a clasp-and-catch connection to prevent unwanted motion. For such a support insert, the tracks will be oriented horizontally across the insole, rather than heel-to-toe, and will be positioned under the arch area. Again, the specific dimensions of the support insert are flexible and can be changed as desired to suit the user's needs, and the specific dimensions of the attachment mechanisms will be based on the dimensions of the support insert.

It may be noted that the modified insole 30 and modified support insert 60, as shown in FIGS. 10 to 13, do not have visible screw holes. The screw holes are omitted in accordance with an embodiment of the invention comprising only a support insert and a modified insole. According to this embodiment, a user may simply insert an insole with a support insert into any shoe. Further, a user may attach a desired support insert to any insole that has been modified to receive that clip. However, it should be clear that adding screw holes to the insole and support insert, and thus facilitating their connection to an overall orthotic system in accordance with another embodiment of the invention, can be easily implemented.

Figure 14:
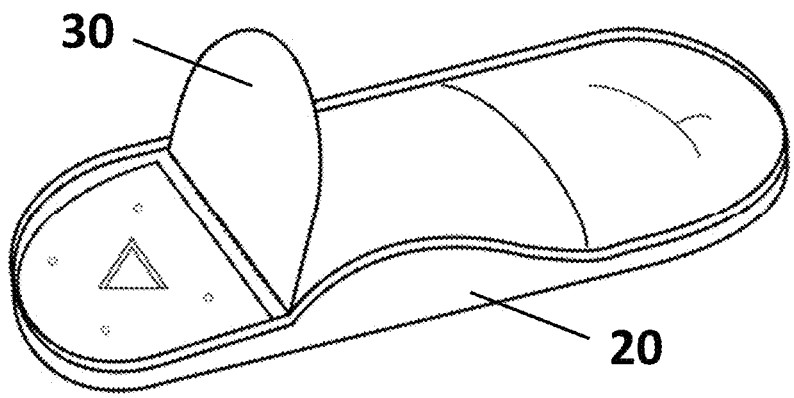
FIG. 14 shows an insole partially attached to a midsole according to one embodiment of the invention, with the heel portion of the insole lifted to show the connection mechanism on the midsole.

FIG. 14 shows an insole 30 on a midsole 20 according to another embodiment of the invention. The heel portion of the insole lifts so that the user can connect an implementation of a heel support insert to the midsole and the underside of the insole. In one implementation, the heel portion of the insole lifts away at a sharp angle relative to the midsole. This sharp lift may be achieved by, e.g., scoring the underside of the insole. However, as would be understood, it is preferable that the top surface of the insole remains substantially smooth. That is, any such scoring is preferably not evident from the top of the insole, to provide a more comfortable experience for the user. FIG. 14 also shows a heel cavity in which the heel support insert can be inserted. The cavity is formed between the heel portion of the insole and the midsole. The cavity further includes at least one recess. In one embodiment of the present invention, the recesses comprise at least one triangular recess surrounded by a plurality of cylindrical recesses.

Figure 15:
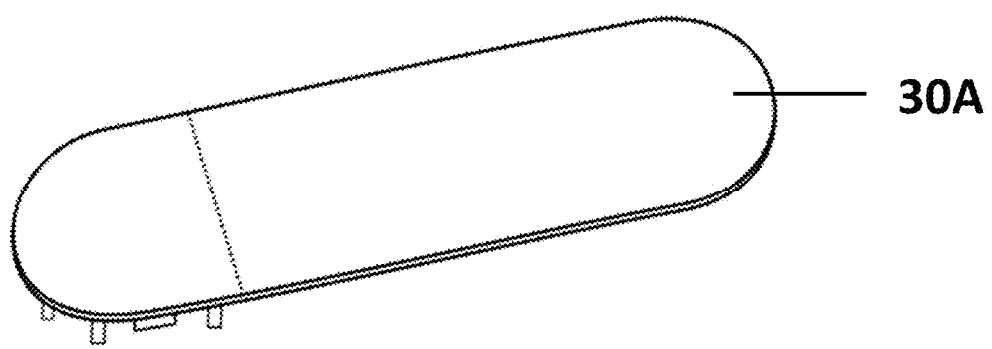
FIG. 15 shows an insole according to the embodiment in FIG. 14.

FIG. 15 shows an insole 30A, modified to clip into a heel support insert 60. As should be clear, the dotted line indicates where the heel portion of the insole would bend away from the midsole when lifted. However, no indication of this bend-point is required to be visible to the user or on the top of the insole. The clips provide a tension fit between the insole, heel support insert, and midsole. The user's body weight helps to secure the tension fit while the insole is in use. The user can remove the heel support insert first by lifting the heel portion of the insole such that the insole detaches from the heel support insert, and then by detaching the heel support insert out of the midsole. A new heel support insert can be connected as described in FIG. 14, or the user can connect the underside of the insole directly to the midsole if a heel support insert is no longer desired. As should be understood, heel support inserts of varying heights may be used as desired. FIG. 15 also shows at least one protrusion on the underside of the heel portion of the insole 30A.

Figure 16:
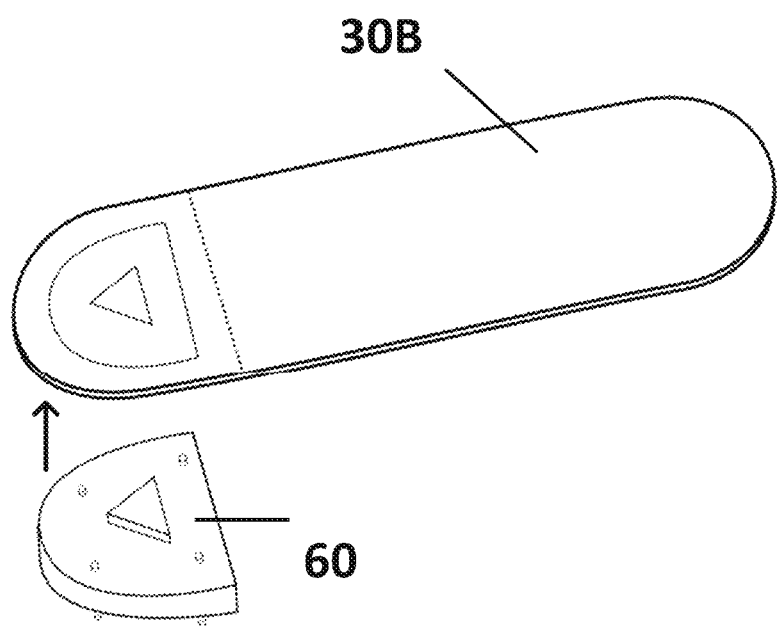
FIG. 16 shows an insole and heel support insert according to another embodiment of the invention.

FIG. 16 shows an insole 30B according to another implementation of the invention, where posts and corresponding recesses exist on the heel support insert 60 and the underside of the insole. As would be clear to a person skilled in the art, the connecting structures between the insole, heel support insert, and midsole can be any type of connecting mechanism. As non-limiting examples, clips, posts, and extrusions with corresponding recesses may be used.

A person understanding this invention may now conceive of alternative structures and embodiments or variations of the above all of which are intended to fall within the scope of the invention as defined in the claims that follow.

I claim:

1. A kit of parts for assembly into a shoe, the kit comprising:
    at least one sole, each of said at least one sole comprising:
        an interchangeable outsole selected from a plurality of interchangeable outsoles;
        an interchangeable midsole selected from a plurality of interchangeable midsoles, said interchangeable midsole comprising an outer shell and a support structure within the outer shell; and
        an interchangeable insole having a heel portion and a forward portion, said heel portion being movable about a score, said score being between said heel portion and said forward portion,
    wherein said interchangeable insole is selected from a plurality of interchangeable insoles;
    at least one interchangeable upper; and
    a plurality of heel support inserts, wherein each heel support insert includes at least one recess and at least one protrusion,
    wherein said interchangeable midsole is for removable attachment to a top side of said interchangeable outsole and said interchangeable insole is for removable attachment to a top side of said interchangeable midsole,
    wherein attaching said interchangeable insole to said top side of said interchangeable midsole forms a heel support cavity between said interchangeable midsole and said interchangeable insole,
    wherein said plurality of heel support inserts is for insertion into said heel support cavity,
    wherein said interchangeable insole comprises at least one protrusion positioned on said heel portion such that said at least one protrusion can be inserted into said at least one recess of each one of said plurality of heel support inserts when said heel support insert is inserted into said heel support cavity,
    wherein a height of said heel portion is adjustable based on preferences of a user,
    wherein said height of said heel portion is adjusted by inserting or removing a number of individual heel support inserts, and
    wherein each of said at least one interchangeable upper is for removable attachment to each of said at least one sole to form said shoe.

2. The kit according to claim 1, wherein said at least one protrusion on said interchangeable insole comprises a plurality of posts and a block.

3. The kit according to claim 2, wherein said plurality of posts is arranged on a periphery of said heel portion and wherein said block is arranged central to said heel portion.

4. The kit according to claim 2, wherein said posts are cylindrical and said block is triangular.

* * * * *